US010681259B2

(12) United States Patent
Ichiki et al.

(10) Patent No.: US 10,681,259 B2
(45) Date of Patent: Jun. 9, 2020

(54) IMAGING APPARATUS, IMAGING METHOD, AND IMAGING SYSTEM (71) Applicant: Sony Corporation, Tokyo (JP)

(72) Inventors: Hiroshi Ichiki, Kanagawa (JP); Isamu Nakao, Tokyo (JP); Tetsuro Kuwayama, Tokyo (JP); Noriyuki Kishii, Kanagawa (JP); Yusaku Nakashima, Tokyo (JP); Takeshi Matsui, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/076,447

(22) PCT Filed: Dec. 9, 2016

(86) PCT No.: PCT/JP2016/086695
§ 371 (c)(1),
(2) Date: Aug. 8, 2018

(87) PCT Pub. No.: WO2017/141524
PCT Pub. Date: Aug. 24, 2017

(65) Prior Publication Data
US 2019/0045112 A1 Feb. 7, 2019

(30) Foreign Application Priority Data
Feb. 18, 2016 (JP) .................... 2016-028762

(51) Int. Cl.
H04N 5/232 (2006.01)
A61B 5/026 (2006.01)
(Continued)

(52) U.S. Cl.
CPC ......... *H04N 5/23212* (2013.01); *A61B 1/043* (2013.01); *A61B 5/0066* (2013.01);
(Continued)

(58) Field of Classification Search
CPC .. H04N 5/235; H04N 9/04551; H04N 5/2256; A61B 1/04
See application file for complete search history.

(56) References Cited

U.S. PATENT DOCUMENTS 8,502,926 B2 * 8/2013 Bilbrey .................... H04N 5/74
348/744
2006/0013544 A1 1/2006 Bouma et al.
(Continued)

FOREIGN PATENT DOCUMENTS

JP 2008-506426 A 3/2008
JP 2010-503475 A 2/2010
(Continued)

OTHER PUBLICATIONS

International Search Report and Written Opinion and English translation thereof dated Mar. 7, 2017 in connection with International Application No. PCT/JP2016/086695.
(Continued)

*Primary Examiner* — Twyler L Haskins
*Assistant Examiner* — Angel L Garces-Rivera
(74) *Attorney, Agent, or Firm* — Wolf, Greenfield & Sacks, P.C.

(57) ABSTRACT

Provided is an imaging technique capable of detecting a focus even in an imaging apparatus of a speckle image. The imaging apparatus includes a coherent light source that irradiates an imaging object with coherent light, an incoherent light source that irradiates the imaging object with incoherent light, a speckle imaging unit that captures a speckle image obtained from scattered light of the imaging object irradiated with the coherent light, a non-speckle imaging unit that captures a non-speckle image obtained from reflected light of the imaging object irradiated with the incoherent light, and a focus detection unit that detects a (Continued)

focus of the speckle imaging unit on the basis of a focal position of the non-speckle imaging unit.

18 Claims, 6 Drawing Sheets

(51) Int. Cl.
| | |
|---|---|
| *G02B 27/48* | (2006.01) |
| *H04N 5/235* | (2006.01) |
| *G02B 7/32* | (2006.01) |
| *A61B 5/00* | (2006.01) |
| *H04N 5/217* | (2011.01) |
| *A61B 1/04* | (2006.01) |
| *G02B 7/28* | (2006.01) |
| *H04N 9/04* | (2006.01) |
| *G02B 7/09* | (2006.01) |
| *G02B 27/00* | (2006.01) |
| *H04N 5/225* | (2006.01) |
| *G02B 23/24* | (2006.01) |
| *A61B 90/00* | (2016.01) |

(52) U.S. Cl.
CPC ............ *A61B 5/0261* (2013.01); *A61B 5/489* (2013.01); *G02B 7/09* (2013.01); *G02B 7/28* (2013.01); *G02B 7/32* (2013.01); *G02B 27/0025* (2013.01); *G02B 27/48* (2013.01); *H04N 5/217* (2013.01); *H04N 5/2256* (2013.01); *H04N 5/2258* (2013.01); *H04N 5/2354* (2013.01); *H04N 9/04517* (2018.08); *A61B 5/0035* (2013.01); *A61B 90/361* (2016.02); *G02B 23/2407* (2013.01)

(56) References Cited

U.S. PATENT DOCUMENTS

| | | |
|---|---|---|
| 2008/0287808 A1 | 11/2008 | Tearney et al. |
| 2015/0142461 A1 | 5/2015 | Darty |

FOREIGN PATENT DOCUMENTS

| | | |
|---|---|---|
| JP | 2013-213695 A | 10/2013 |
| JP | 2016-504563 A | 2/2016 |
| WO | WO 2006-014392 A1 | 2/2006 |
| WO | WO 2008/033909 A2 | 3/2008 |
| WO | WO 2014-063117 A1 | 4/2014 |

OTHER PUBLICATIONS

International Preliminary Report on Patentability and English translation thereof dated Aug. 30, 2018 in connection with International Application No. PCT/JP2016/086695.

* cited by examiner

IMAGING APPARATUS, IMAGING METHOD, AND IMAGING SYSTEM

CROSS-REFERENCE TO RELATED APPLICATIONS

This application claims the benefit under 35 U.S.C. § 371 as a U.S. National Stage Entry of International Application No. PCT/JP2016/086695, filed in the Japanese Patent Office as a Receiving Office on Dec. 9, 2016, which claims priority to Japanese Patent Application Number JP 2016-028762, filed in the Japanese Patent Office on Feb. 18, 2016, each of which is hereby incorporated by reference in its entirety.

TECHNICAL FIELD

The present technology relates to an imaging apparatus and, more particularly, to an imaging apparatus, an imaging method, and an imaging system capable of detecting a focus for capturing a speckle image.

BACKGROUND ART

In the related art, in order to grasp the shape, structure, and the like of a biological sample such as a blood vessel or a cell, an imaging apparatus and an imaging method using an optical method have been developed (refer to Patent Literature 1).

In an imaging system disclosed in Patent Literature 1, an interference light image by light obtained by reflection of light from a light emitting unit on an object and interference is captured at a first timing, and a luminescent image of the light emitted from the object is captured at a second timing.

On the other hand, in an imaging technique using an optical method in the case of using a flow path such as a blood vessel as an imaging object, there is a concern that occurrence of various noises may cause detection accuracy to deteriorate. As one of the noises, speckle is known. The speckle is a phenomenon in which a spot-like swaying pattern appears on an irradiated surface depending on an uneven shape of the irradiated surface. In recent years, techniques have also been developed with respect to a method of imaging a flow path such as a blood vessel by using speckle which is one of the noises.

Speckle is a random interference/diffraction pattern due to scattering or the like in an optical path. In addition, the magnitude of speckle is represented by an index called speckle contrast which is a value obtained by dividing the standard deviation of the intensity distribution by the average of the intensity distribution. When the imaging object irradiated with coherent light is observed by using an imaging optical system, the speckle caused by scattering of the imaging object is observed on the image plane. Then, when the imaging object moves or changes in shape, a random speckle pattern corresponding to the movement or change is observed.

When a light scattering fluid such as blood is observed, the speckle pattern changes at every moment according to the change in fine shape caused by the flow. At that time, when an imaging element is arranged on the image plane and the fluid is imaged with an exposure time sufficiently longer than the change of the speckle pattern, the speckle contrast of a portion in which the blood is flowing, that is, a portion of the blood vessel is reduced in time average. Angiography can be performed by using such a change in speckle contrast.

CITATION LIST

Patent Literature

Patent Literature 1: JP-A-2009-136396

DISCLOSURE OF INVENTION

Technical Problem

In the imaging apparatus using such speckles, since the speckle pattern is measured by a monocular camera, the focus of the imaging cannot be identified as compared with the normal bright field imaging, and as a result, the speckle image with the low resolution is captured. In addition, there are problems of large particle noise caused by speckle, incapability of acquiring depth information of an image to be captured, and the like.

In view of this, a main object of the present technology is to provide an imaging technique capable of detecting a focus even in an imaging apparatus for a speckle image.

Solution to Problem

According to the present technology, there is provided an imaging apparatus including: a coherent light source that irradiates an imaging object with coherent light; an incoherent light source that irradiates the imaging object with incoherent light; a speckle imaging unit that captures a speckle image obtained from scattered light of the imaging object irradiated with the coherent light; a non-speckle imaging unit that captures a non-speckle image obtained from reflected light of the imaging object irradiated with the incoherent light; and a focus detection unit that detects a focus of the speckle imaging unit on the basis of a focal position of the non-speckle imaging unit.

In addition, the imaging apparatus according to the present technology may further include: a focus adjustment unit that adjusts a focal length of the speckle imaging unit with respect to a focus of the non-speckle imaging unit; and a display unit that displays the speckle image captured on the basis of the focus adjusted by the focus adjustment unit.

The imaging apparatus according to the present technology may further include an aberration correction unit that corrects aberration occurring between the non-speckle imaging unit and the speckle imaging unit. In the imaging apparatus, the aberration correction unit may be configured to correct chromatic aberration.

The imaging apparatus according to the present technology may further include: a region-of-interest specification unit that specifies an arbitrary region of interest in the non-speckle image captured by the non-speckle imaging unit; and a light irradiation adjustment unit that adjusts an irradiation position of the coherent light source on the basis of specification information of the region of interest by the region-of-interest specification unit.

Furthermore, according to the present technology, there is also provided an imaging system including: a coherent light source that irradiates an imaging object with coherent light; an incoherent light source that irradiates the imaging object with incoherent light; a speckle imaging device that captures a speckle image obtained from scattered light of the imaging object irradiated with the coherent light; a non-speckle imaging device that captures a non-speckle image obtained from reflected light of the imaging object irradiated with the incoherent light; and a focus detection device that detects a focus of the speckle imaging device on the basis of a focal position of the non-speckle imaging device.

The imaging system may further include a focus adjustment device that adjusts a focal length of the speckle imaging device with respect to a focus of the non-speckle imaging device; and a display device that displays the speckle image captured on the basis of the focus adjusted by the focus adjustment device.

The imaging system according to the present technology may further include an aberration correction device that corrects aberration occurring between the non-speckle imaging device and the speckle imaging device. In the imaging system, the aberration correction device may be configured to correct chromatic aberration.

The imaging system according to the present technology may further include: a region-of-interest specification device that specifies an arbitrary region of interest in the non-speckle image captured by the non-speckle imaging device; and a light irradiation adjustment device that adjusts an irradiation position of the coherent light source on the basis of specification information of the region of interest by the region-of-interest specification device.

According to the present technology, there is also provided an imaging method including: a coherent light irradiating step of irradiating an imaging object with coherent light; an incoherent light irradiating step of irradiating the imaging object with incoherent light; a speckle imaging step of capturing a speckle image obtained from scattered light of the imaging object irradiated with the coherent light; a non-speckle imaging step of capturing a non-speckle image obtained from reflected light of the imaging object irradiated with the incoherent light; and a focus detecting step of detecting a focus for capturing the speckle image on the basis of a focal position in the non-speckle imaging step.

Advantageous Effects of Invention

According to the present technology, it is possible to detect a focus in an imaging technique for a speckle image, and as a result, it is possible to obtain a speckle image with high resolution.

In addition, the effects described herein are not necessarily limited and may be any of the effects that are intended to be described in the present technology.

MODE(S) FOR CARRYING OUT THE INVENTION

Suitable embodiments for implementing the present technology will be described below with reference to the drawings. Each embodiment described below illustrates an example of a representative embodiment of the present technology, so that the scope of the present technology is not to be narrowly interpreted by the embodiments. In addition, the description will be made in the following order.

Figure 1:
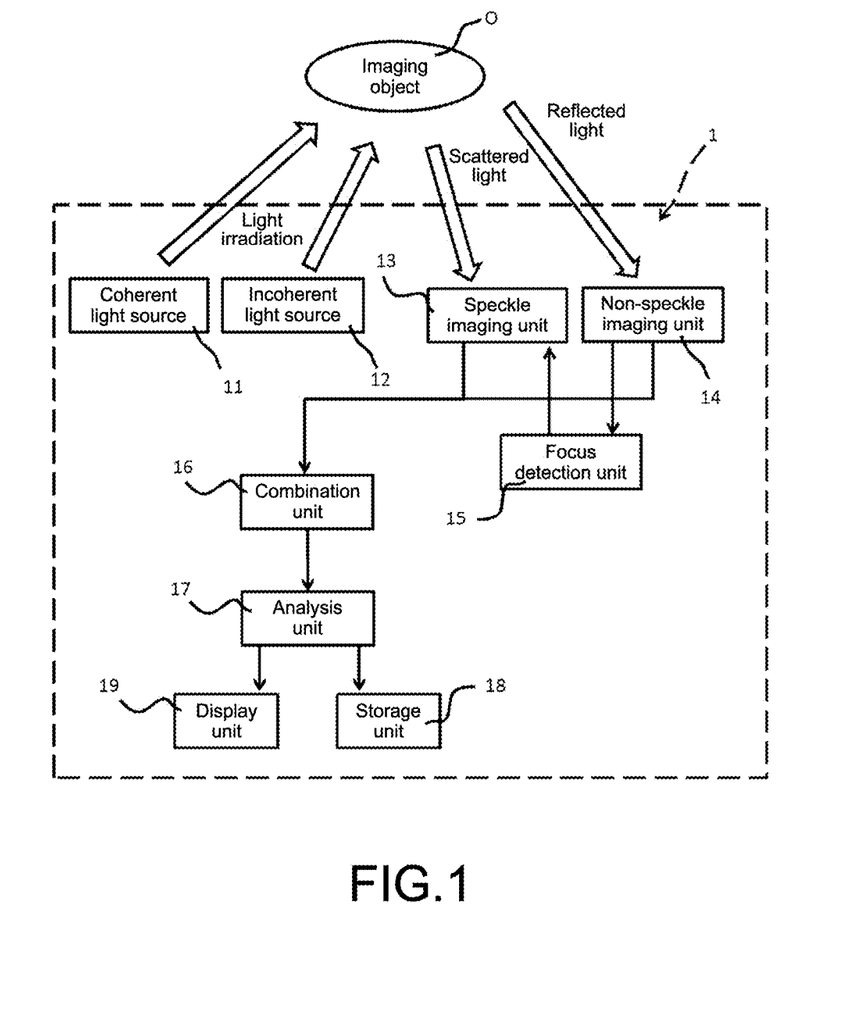
FIG. 1 is a schematic conceptual diagram schematically illustrating a concept of a first embodiment of an imaging apparatus according to the present technology.

1. Imaging Apparatus according to First Embodiment
(1) Coherent Light Source
(2) Incoherent Light Source
(3) Speckle Imaging Unit
(4) Non-Speckle Imaging Unit
(5) Focus Detection Unit
(6) Combination Unit
(7) Analysis Unit
(8) Storage Unit
(9) Display Unit
(10) Imaging Object
2. Imaging Apparatus according to Second Embodiment
(1) Focus Adjustment Unit
3. Imaging Apparatus according to Third Embodiment
(1) Aberration Correction Unit
4. Imaging Apparatus according to Fourth Embodiment
(1) Region-Of-Interest Specification Unit
(2) Light Irradiation Adjustment Unit
5. Imaging System according to Present Technology
(1) Coherent Light Source
(2) Incoherent Light Source
(3) Speckle Imaging Device
(4) Non-Speckle Imaging Device
(5) Focus Detection Device
(6) Combination Device
(7) Analysis Device
(8) Storage Device
(9) Display Device
(10) Focus Adjustment Device
(11) Aberration Correction Device
(12) Region-Of-Interest Specification Device
(13) Light Irradiation Adjustment Device
6. Imaging Method according to First Embodiment
(1) Coherent Light Irradiating Step
(2) Incoherent Light Irradiating Step
(3) Speckle Imaging Step
(4) Non-Speckle Imaging Step
(5) Focus Detecting Step
(6) Combining Step
(7) Analyzing Step
(8) Storing Step
(9) Displaying Step
(10) Focus Adjusting Step
(11) Aberration Correcting Step
(12) Region-Of-Interest Specifying Step
(13) Light Irradiation Adjusting Step 1. Imaging Apparatus According to First Embodiment FIG. 1 is a schematic conceptual diagram schematically illustrating a first embodiment of an imaging apparatus according to the present technology. The imaging apparatus 1 according to the first embodiment at least includes a coherent light source 11, an incoherent light source 12, a speckle imaging unit 13, a non-speckle imaging unit 14, and a focus detection unit 15. In addition, as necessary, the imaging apparatus may further include a combination unit 16, an analysis unit 17, a storage unit 18, a display unit 19, and the like. Each component will be described in detail below.

(1) Coherent Light Source

The coherent light source 11 irradiates an imaging object O with coherent light. The coherent light emitted from the coherent light source 11 denotes light in which the phase relationship between light waves at arbitrary two points in a light flux is invariable and constant in terms of time and, thus, even in the case of dividing the light flux by an arbitrary method and, after that, providing a large optical path difference and overlaying the divided light fluxes again, perfect coherency is exhibited.

The type of the coherent light source 11 is not particularly limited as long as the effect of the present technology is not impaired. As an example, laser light and the like may be exemplified. As the coherent light source 11 that emits laser light, an argon ion (Ar) laser, a helium-neon (He—Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(2) Incoherent Light Source

The incoherent light source 12 irradiates the imaging object O with incoherent light. The incoherent light denotes light which hardly has coherency like object light (object wave). Herein, it is desirable that the wavelength of the incoherent light is approximately equal to the wavelength of the coherent light emitted from the coherent light source 11. Therefore, when the incoherent light is irradiated, it is desirable to adopt a configuration capable of adjusting the wavelength of the incoherent light using a bandpass filter.

The type of the incoherent light source 12 is not particularly limited as long as the effect of the present technology is not impaired. As an example, a light emitting diode or the like may be exemplified. As other light sources, a xenon lamp, a metal halide lamp, a high pressure mercury lamp, and the like may be exemplified.

(3) Speckle Imaging Unit

The imaging apparatus 1 according to the present technology includes a speckle imaging unit 13. In this speckle imaging unit 13, speckle imaging is performed on the basis of scattered light obtained from the imaging object O irradiated with the coherent light. More specifically, speckle imaging is performed on the basis of the focus detected by the focus detection unit 15.

The imaging method performed by the speckle imaging unit 13 is not particularly limited as long as the effect of the present technology is not impaired, and one or two or more known imaging methods may be selected and used freely in combination. For example, an imaging method using an imaging element such as a charge coupled device (CCD) or a complementary metal oxide semiconductor (CMOS) sensor may be exemplified.

In addition, the speckle imaging unit 13 may measure the luminance distribution of the speckle in the captured image. Herein, when an object illuminated by using coherent light is observed by the imaging optical system, speckle caused by scattering of the object on the image plane is observed. In the speckle imaging unit 13, the luminance distribution of the speckle in the captured image is measured using, for example, a luminance meter. In addition, it is possible to calculate the speckle luminance distribution from an image captured from an imaging element such as a CCD or a CMOS.

The method of measuring the luminance distribution is not particularly limited as long as the effect of the present technology is not impaired, and one or two or more known calculation methods may be selected and used freely in combination.

In the speckle imaging unit 13, for example, an image or the like in which a pseudo blood vessel through which pseudo blood flows is mapped on the basis of the speckle luminance distribution is generated. Herein, since the speckle is a random interference/diffraction pattern as described above, when the scattering fluid such as blood moves or changes with time, the speckle also varies with time. For this reason, it is possible to observe the boundary between the fluid and other portions.

Note that, in order to clarify the portion where speckle occurs, the speckle imaging unit 13 may have a configuration where, for example, equalization is performed by using a plurality of speckle images to reduce irregularity of the speckle image.

(4) Non-Speckle Imaging Unit

The imaging apparatus 1 according to the present technology includes a non-speckle imaging unit 14. In this non-speckle imaging unit 14, the bright field image is captured on the basis of the reflected light obtained from the imaging object O irradiated with incoherent light. Herein, since the incoherent light is light which hardly exhibits coherency, in the captured image based on the incoherent light, speckle which is a random interference/diffraction pattern does not occur. Hereinafter, for the convenience of description, a captured image where speckle does not occur is referred to as a "non-speckle image". Since the imaging method performed in the non-speckle imaging unit 14 is the same as the imaging method performed by the speckle imaging unit 13, the description thereof is omitted herein.

(5) Focus Detection Unit

The imaging apparatus 1 according to the present technology includes a focus detection unit 15 that detects a focus for capturing the speckle image.

Figure 2:
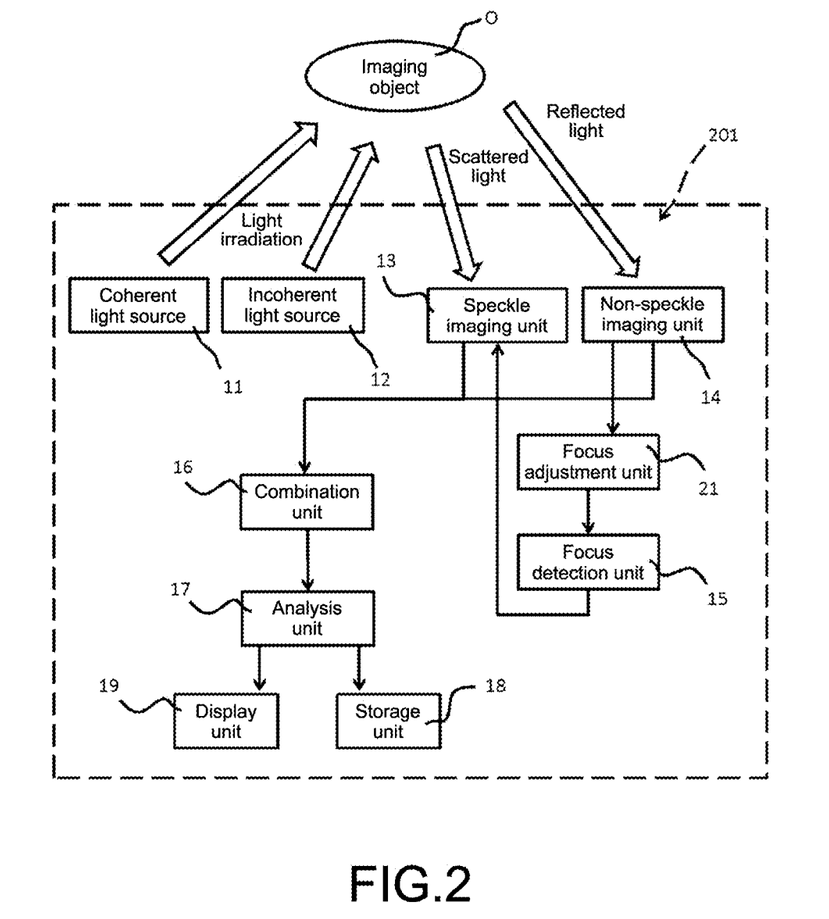
FIG. 2 is a schematic conceptual diagram illustrating a technical principle of the imaging apparatus illustrated in FIG. 1.

Since speckle is a random interference/diffraction pattern, it is difficult to identify the focus in the case of imaging the speckle. On the other hand, in a case where the image forming system is off-focused to the front side or the rear side and the imaging object O is deviated in the vertical direction from the optical axis, an interference light path which starts from one point of the imaging object O to form one speckle shape passes through a point near the optical axis on the imager with respect to the principal ray of the image forming system in the case of being off-focused to the front side and passes through a point away from the optical axis in the case of being off-focused to the rear side. As a result, in a case where the focal position for capturing the speckle image is shifted toward the user side or the rear side with respect to the focus at the time of capturing the non-speckle image, that is, the bright field image, the speckle moves in the same direction as that of the moving body or in a direction different from that of the moving body with respect to the moving body projected on the bright field image. In the following description, this phenomenon will be referred to as a "speckle correlation phenomenon".

On the basis of the speckle correlation phenomenon, the focus detection unit 15 detects the focus of the speckle imaging unit 13. More specifically, first, as a first step, the focal position of the speckle imaging unit 13 is arranged on the further front side of the user than the focal position of the non-speckle image, and the moving direction of the speckle is identified. Next, as a second step, the focal position of the speckle imaging unit 13 is arranged on the further rear side of the user than the focal position of the non-speckle image, and the moving direction of the speckle is identified. After that, while the focal position of the speckle imaging unit 13 arranged on the front side or the rear side is gradually brought closer to the focal position of the non-speckle imaging unit 14, a focal position at which the speckle does not move with respect to the moving body on the bright field image is detected.

In this manner, the focus detection unit 15 can detect the focus of the speckle image where the speckle does not move on the image by using the correlation phenomenon of the speckle.

Herein, the detecting method is merely an example, and in the above-described method, the second step is performed after the first step. However, the first step may be performed after the second step.

(6) Combination Unit

The imaging apparatus 1 according to the present technology includes a combination unit 16. The combination unit 16 combines the speckle image captured by the speckle imaging unit 13 and the non-speckle image captured by the non-speckle imaging unit 14. Specifically, a speckle combined image is generated by superimposing the image information of the non-speckle image and the image information of the speckle image.

Note that the method of generating the speckle combined image is not particularly limited, and a known method may be adopted.

(7) Analysis Unit

The imaging apparatus 1 according to the present technology may include an analysis unit 17 as necessary. The analysis unit 17 analyzes the state of the imaging object O by using the speckle combined image generated by the combination unit 16.

Herein, the analysis unit 17 may also analyze the moving speed of the speckle by using the correlation phenomenon of the speckles observed when the focus detection unit 15 detects the focus.

That is, as described above, in the speckle correlation phenomenon, the speckle moves relative to the moving body on the bright field image. For this reason, the analysis unit 17 may be configured to observe the moving image in the state where the focal position of the speckle imaging unit 13 is shifted from the focal position of the bright field image and to measure the moving speed of the speckle.

In such a case, for example, in a case where the imaging object O is a blood vessel, when the scattering fluid such as blood moves or changes with time, the speckle also varies with time accordingly. Therefore, the speed of the blood flow can be measured by the analysis unit 17.

Note that the analysis unit 17 is not necessarily included in the imaging apparatus 1 according to the present technology, and the state of the imaging object O may also be analyzed by using an external analysis device or the like.

(8) Storage Unit

The imaging apparatus 1 according to the present technology may further include a storage unit 18 that stores the speckle image captured by the speckle imaging unit 13, the non-speckle image captured by the non-speckle imaging unit 14, the speckle combined image generated by the combination unit 16, the focus of the speckle image detected by the focus detection unit 15, the analysis result analyzed by the analysis unit 17, and the like.

This storage unit 18 is not necessarily included in the imaging apparatus 1 according to the present technology, but the imaging apparatus may be connected to, for example, an external storage device to store the speckle image and the like.

(9) Display Unit

The imaging apparatus 1 according to the present technology may further include a display unit 19 that displays the speckle image captured by the speckle imaging unit 13, the non-speckle image captured by the non-speckle imaging unit 14, the combined image generated by the combination unit 16, the analysis result analyzed by the analysis unit 17, and the like. In addition, the display unit 19 may display the luminance distribution measured by the speckle imaging unit 13 and the non-speckle imaging unit 14 so as to be superimposed on the speckle image. The display unit 19 is not necessarily included in the imaging apparatus 1 according to the present technology, and light irradiation may be performed on the imaging object O by using, for example, an external monitor or the like.

(10) Imaging Object

Although the imaging apparatus 1 according to the present technology may set various objects as the imaging objects, the imaging apparatus 1 can be suitably used for imaging an object containing, for example, a fluid as the imaging object O. Due to the nature of the speckle, the speckle is not easily generated from the fluid. For this reason, when the object containing a fluid is imaged by using the imaging apparatus 1 according to the present technology, a boundary between the fluid and other portions, a flow speed of the fluid and the like can be obtained.

More specifically, a biological tissue may be exemplified as an imaging object O, and blood may be exemplified as a fluid. For example, when the imaging apparatus 1 according to the present technology is mounted on a surgical microscope, a surgical endoscope, or the like, surgery can be performed while identifying the position of a blood vessel. Therefore, it is possible to carry out safer and highly accurate surgery, and thus, it is possible to contribute to further development of medical technology.

In the imaging apparatus 1 according to the first embodiment as described above, since the focus detection unit 15 can detect the focus for capturing the speckle image, it is possible to acquire the speckle image with high resolution.

In addition, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue (for example, the heart or the like).

2. Imaging Apparatus According to Second Embodiment

FIG. 2 is a schematic conceptual diagram illustrating an imaging apparatus according to a second embodiment to which the present technology can be applied.

The imaging apparatus 201 according to the second embodiment is different from the imaging apparatus 1 according to the first embodiment in that a focus adjustment unit 21 that adjusts a focal length of the speckle imaging unit is included and the display unit 19 displays the speckle image, which is adjusted in terms of the focus by the focus adjustment unit 21 and, as a result, is captured.

On the other hand, the embodiments are the same in that at least the coherent light source 11, the incoherent light source 12, the speckle imaging unit 13, the non-speckle imaging unit 14, and the focus detection unit 15 are included, and furthermore, the embodiments are the same in that the combination unit 16, the analysis unit 17, and the storage unit 18 may be included as necessary.

Therefore, in the following description of the imaging apparatus 201 according to the second embodiment, the description of the configuration common to the imaging apparatus 1 according to the first embodiment will be omitted. Hereinafter, the focus adjustment unit 21 will be described.

(1) Focus Adjustment Unit

The imaging apparatus 201 according to the second embodiment includes a focus adjustment unit 21. The focus adjustment unit 21 performs a process of changing a focal length of the speckle imaging unit 13 at the stage of detecting the focus when the focus detection unit 15 captures the speckle image.

Specifically, the process performed by the focus detection unit 15, that is, the process of moving the focal position of the speckle imaging unit 13 relative to the focal position of the non-speckle imaging unit 14 is performed. For example, an operation of arranging the focal position of the speckle imaging unit 13 on the further front side of the user than the focal position of the non-speckle image or an operation of arranging the focal position of the speckle imaging unit 13 on the further rear side of the user than the focal position of the non-speckle image is performed.

In addition, in the imaging apparatus 201 according to the second embodiment, the focus adjusted by the focus adjustment unit 21 is input to the speckle imaging unit 13 through the focus detection unit 15, and thus, the speckle imaging unit 13 captures the speckle image on the basis of the input information.

Then, finally, the speckle image captured on the basis of the detected focus is displayed by the display unit 19. In addition, the display unit 19 is configured to display an image in the state where speckle is moving relative to a moving body on the imaging object O observed in the process stage of the focus adjustment unit 21.

In the imaging apparatus 201 according to the second embodiment as described above, since the focus adjustment unit 21 is included, and the display unit 19 is configured to display the speckle image captured on the basis of the focus detected by the focus adjustment unit 21, it is possible to accurately grasp the moving direction of speckle with respect to the moving body on the bright field image with visual observation by using the correlation phenomenon of the speckle.

As a result, for example, in the case of imaging a blood vessel, it is possible to accurately grasp the flowing direction of blood corpuscles and to grasp the type of blood vessel such as whether the imaged blood vessel is an artery or a vein.

3. Imaging Apparatus According to Third Embodiment

Figure 3:
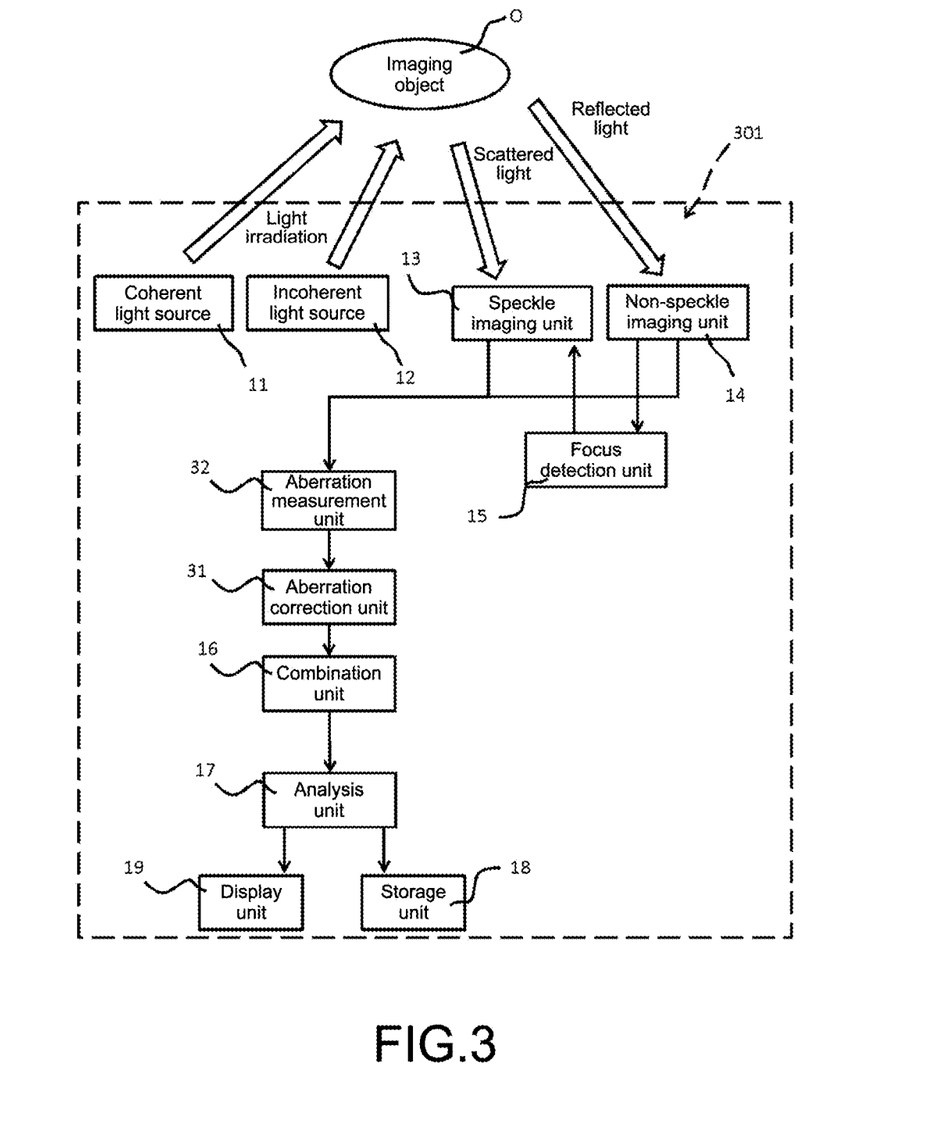
FIG. 3 is a schematic conceptual diagram schematically illustrating a concept of a second embodiment of the imaging apparatus according to the present technology.

Next, an imaging apparatus 301 according to a third embodiment to which the present technology is applied will be described with reference to FIG. 3. FIG. 3 is a schematic conceptual diagram of the imaging apparatus 301 according to the third embodiment.

The imaging apparatus 301 according to the third embodiment is different from the imaging apparatus 1 according to the first embodiment in that an aberration correction unit 31 is provided. On the other hand, the embodiments are the same in that at least the coherent light source 11, the incoherent light source 12, the speckle imaging unit 13, the non-speckle imaging unit 14, and the focus detection unit 15 are included, and furthermore, the embodiments are the same in that the combination unit 16, the analysis unit 17, the storage unit 18, the display unit 19, and the focus adjustment unit 21 may be included as necessary.

For this reason, in the following description of the imaging apparatus 301 according to the third embodiment, the description of the configuration common to the imaging apparatus 1 according to the first embodiment will be omitted. Hereinafter, the aberration correction unit 31 will be described.

(1) Aberration Correction Unit

In the imaging apparatus 301 according to the third embodiment, a speckle image is captured by the speckle imaging unit 13, and a non-speckle image is captured by the non-speckle imaging unit 14. That is, the imaging apparatus 301 constitutes a compound eye imaging apparatus. Therefore, aberration occurs between the speckle image and the non-speckle image in the imaging apparatus 301.

In such a case, in the case of generating a combined image including the non-speckle image and the speckle image superimposed on each other, it is necessary to eliminate the aberration as much as possible. The aberration correction unit 31 performs a process of correcting the aberration.

The type of aberration that can be corrected by the aberration correction unit 31 is not particularly limited, and well-known aberrations such as spherical aberration, coma aberration, astigmatism, chromatic aberration (axial chromatic aberration, magnification chromatic aberration), wavefront aberration, field curvature, and deformed image may be corrected. Since the imaging apparatus according to the present technology uses two types of light sources having different wavelengths, it is desirable that the imaging apparatus is configured so as to correct, particularly, chromatic aberration among these aberrations.

Herein, the method of correcting the aberration is not particularly limited, and a known method may be adopted. For example, a method using a deformable mirror, a method of correcting the acquired image itself, or the like may be used.

The imaging apparatus 301 according to the third embodiment may include an aberration measurement unit 32 that measures the aberration. In the aberration measurement unit 32, aberrations may be measured by using a known method. For example, a method of analyzing interference fringes by optical interference measurement may be considered to be adopted.

Then, the aberration measured by the aberration measurement unit 32 is input to the aberration correction unit 31, and thus, the aberration correction unit 31 is configured to correct the aberration on the basis of the input information.

In the imaging apparatus 301 according to the third embodiment having the aberration correction unit 31, since aberration occurring between the speckle image and the non-speckle image, particularly chromatic aberration, can be corrected by the aberration correction unit 31, it is possible to improve the resolution of the speckle image and the resolution of the non-speckle image and also to improve the resolution of the combined image including the speckle image and the non-speckle image.

As a result, for example, in the case of imaging a blood vessel in which blood is flowing, it is possible to accurately observe the relative position of the blood vessel to the biological tissue.

4. Imaging Apparatus According to Fourth Embodiment

Figure 4:
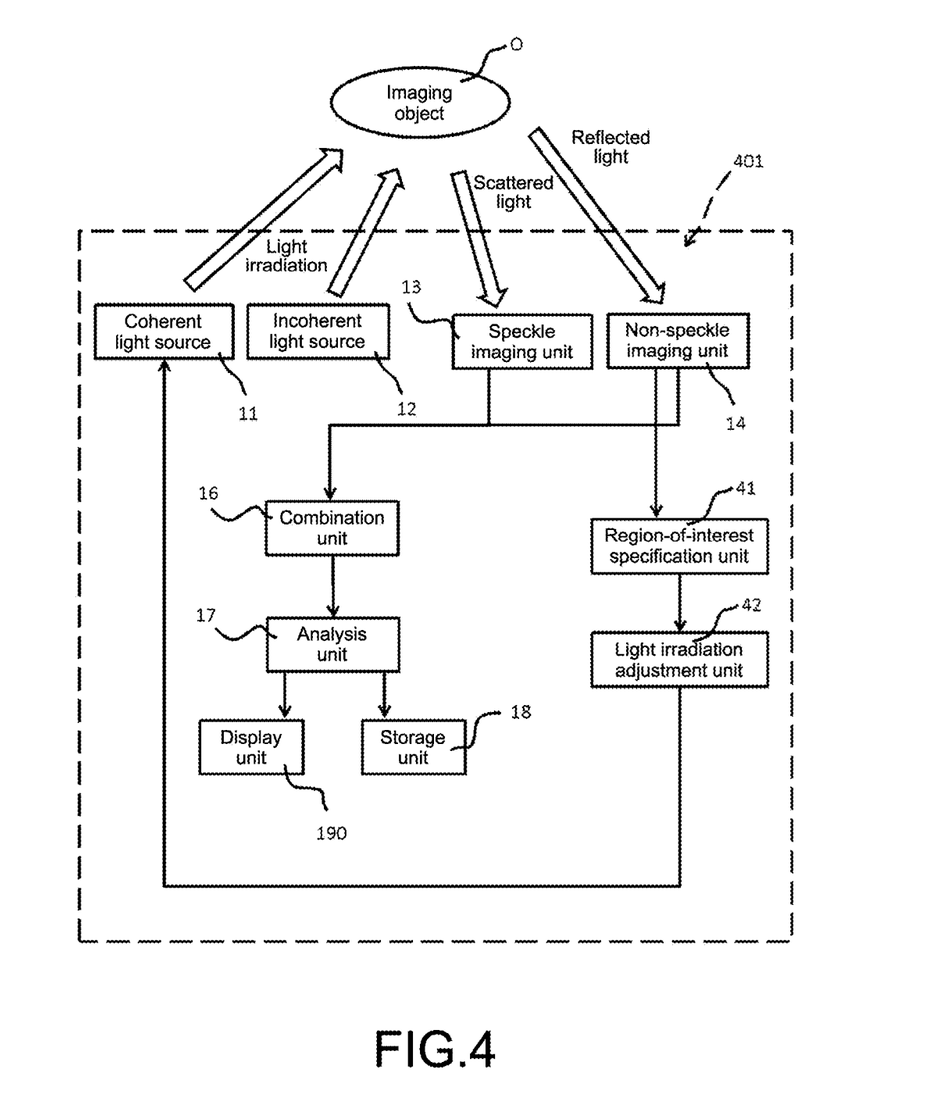
FIG. 4 is a schematic conceptual diagram schematically illustrating a concept of a third embodiment of the imaging apparatus according to the present technology.
Figure 5:
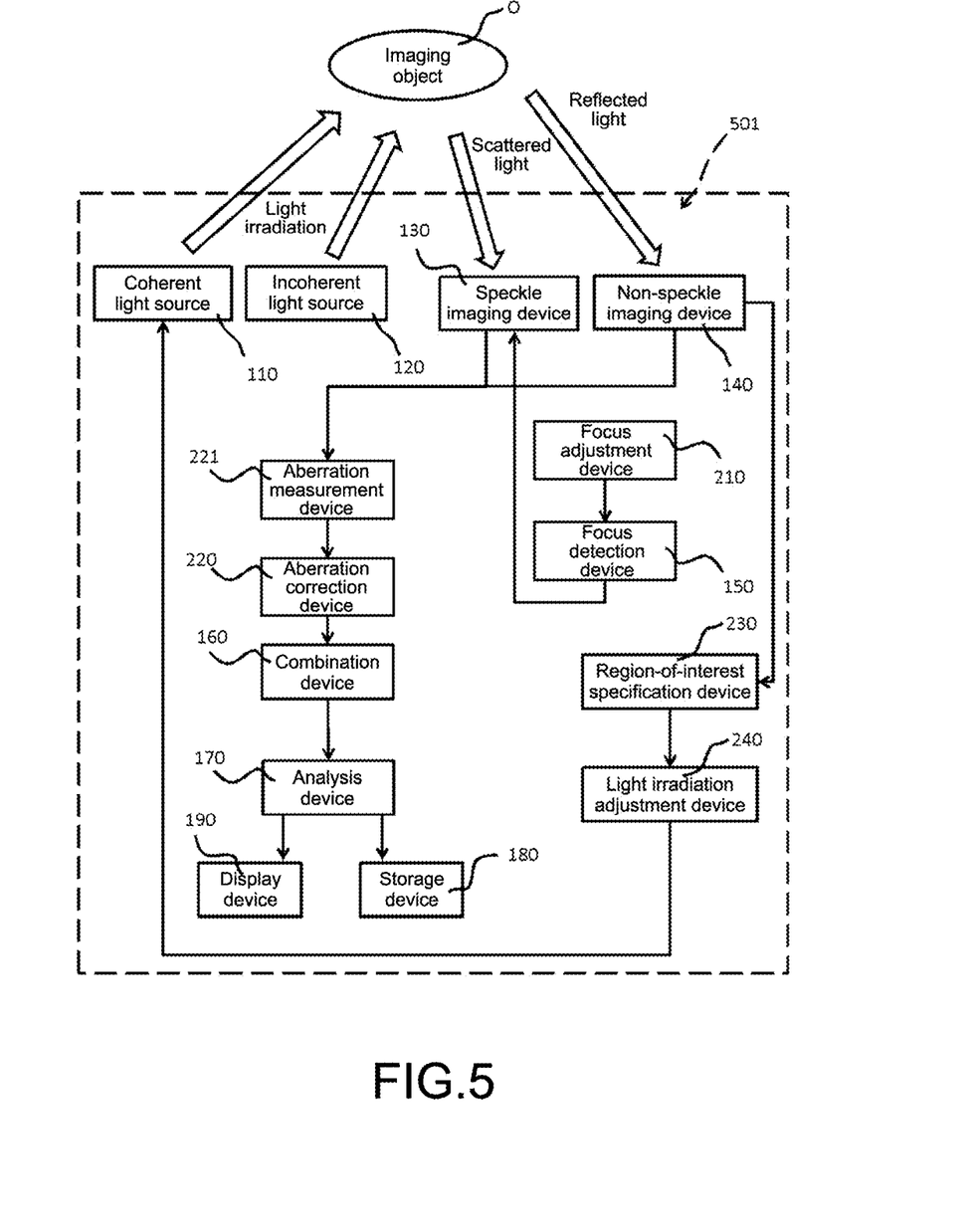
FIG. 5 is a schematic conceptual diagram schematically illustrating a concept of an imaging system according to the present technology.

Next, an imaging apparatus 401 according to a fourth embodiment to which the present technology is applied will be described with reference to FIG. 4. FIG. 3 is a schematic conceptual diagram of the imaging apparatus 401 according to the fourth embodiment.

The imaging apparatus 401 according to the fourth embodiment is different from the imaging apparatus 1 according to the first embodiment in that a region-of-interest specification unit 41 and a light irradiation adjustment unit 42 are provided. On the other hand, the embodiments are the same in that at least the coherent light source 11, the incoherent light source 12, the speckle imaging unit 13, the non-speckle imaging unit 14, and the focus detection unit 15 are included, and furthermore, the embodiments are the same in that the combination unit 16, the analysis unit 17, the storage unit 18, the display unit 19, the focus adjustment unit 21, the aberration correction unit 31 and the like may be included as necessary.

For this reason, in the following description of the imaging apparatus 401 according to the fourth embodiment, the description of the configuration common to the imaging apparatus 1 according to the first embodiment will be omitted. Hereinafter, the region-of-interest specification unit 41 and the light irradiation adjustment unit 42 will be described.

(1) Region-Of-Interest Specification Unit

The imaging apparatus 401 according to the fourth embodiment includes a region-of-interest specification unit 41 for specifying a region to be observed by a user from a non-speckle image.

More specifically, the region-of-interest specification unit 401 identifies the non-speckle image displayed by the display unit 19 and selects an arbitrary region in which the user is interested in observation. After that, the region-of-interest specification unit 41 detects the position information of the region of interest selected by the user. In addition, on the basis of the information on the detected region of interest, the region of interest within the imaging object O illustrated on the non-speckle image is specified.

Note that the specifying method performed by the region-of-interest specification unit 41 is not particularly limited, and a known method may be used. For example, it is considered that the region-of-interest specification unit 41 detects the position information of each pixel in the horizontal direction and the vertical direction of the combined image including the region of interest selected by the user and specifies the region of interest on the basis of the detected position information.

(2) Light Irradiation Adjustment Unit

The imaging apparatus 401 according to the fourth embodiment includes a light irradiation adjustment unit 42 for irradiating the region of interest specified by the region-of-interest specification unit 41 with light.

Specifically, the configuration of the light irradiation adjustment unit 42 is not particularly limited, and the light irradiation adjustment unit 42 is configured as, for example, a biaxial actuator that moves the incoherent light source 12 in horizontal and vertical directions and stops the incoherent light source 12.

Then, the light irradiation adjustment unit 42 adjusts the irradiation direction by moving the incoherent light source 12 so that the region of interest is irradiated with the incoherent light on the basis of the position information of the region of interest detected by the region-of-interest specification unit 41.

In the imaging apparatus 401 according to the fourth embodiment including the region-of-interest specification unit 41 and the light irradiation adjustment unit 42, since only the region in which the user is interested can be irradiated with the incoherent light, it is possible to maximize the intensity distribution of the speckle in the region of interest in the speckle image to be captured. As a result, it is possible to generate the speckle image and, hence, the combined image with high resolution. Since the irradiation range of the incoherent light can be limited to the range of the region of interest, that is, the minimum necessary illumination intensity can be obtained, coherency of the incoherent light can be maintained constant. In addition, it is possible to reduce the adverse effect on the user due to irradiation with the incoherent light which is high in output density and harmful to the human body.

5. Imaging System

Figure 6:
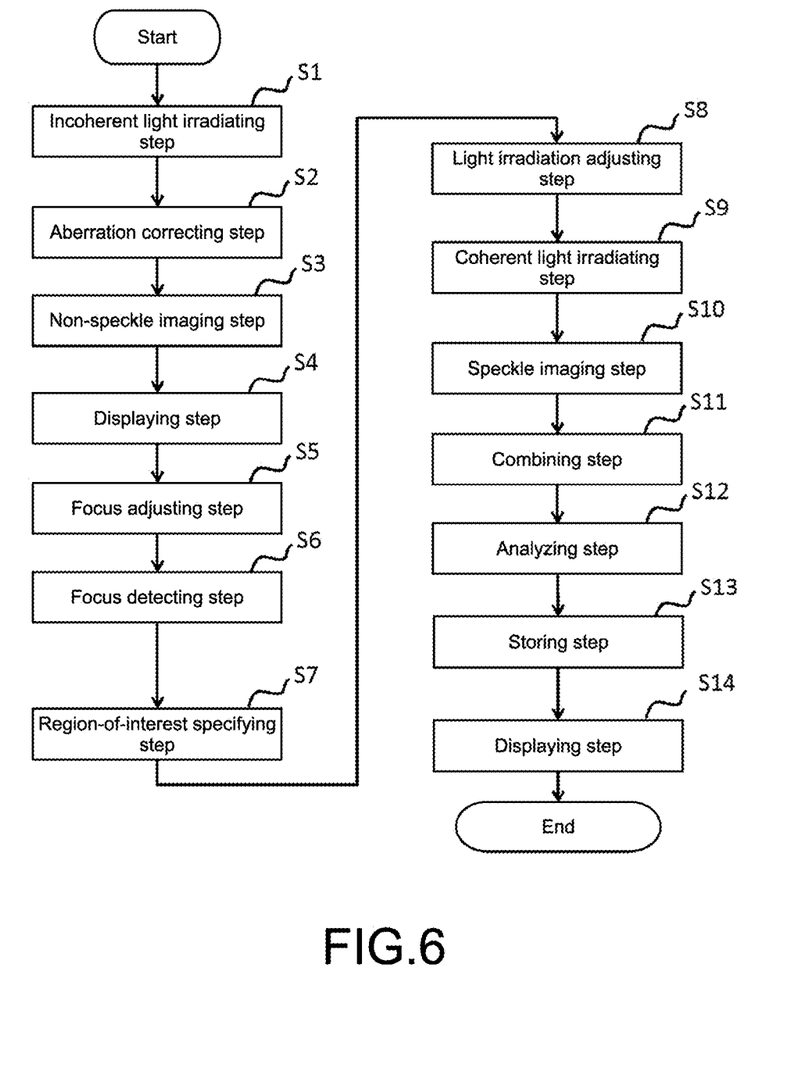
FIG. 6 is a flowchart of an imaging method according to the present technology.

The present technology also provides an imaging system. FIG. 6 is a schematic conceptual diagram schematically illustrating an imaging system 501 according to the first embodiment of the present technology. The imaging system 501 includes at least a coherent light source 110, an incoherent light source 120, a speckle imaging device 130, a non-speckle imaging device 140, and a focus detection device 150. In addition, as necessary, the imaging system 501 may further include a combination device 160, an analysis device 170, a storage device 180, a display device 190, a focus adjustment device 210, an aberration correction device 220, a region-of-interest specification device 230, and a light irradiation adjustment device 240. Each device will be described below.

(1) Coherent Light Source

The coherent light source 110 irradiates the imaging object O with coherent light. The coherent light emitted from the coherent light source 110 denotes light in which the phase relationship between light waves at arbitrary two points in a light flux is invariable and constant in terms of time and, thus, even in the case of dividing the light flux by an arbitrary method and, after that, providing a large optical path difference and overlaying the divided light fluxes again, perfect coherency is exhibited.

The type of the coherent light source 110 is not particularly limited as long as the effect of the present technology is not impaired. As an example, laser light and the like may be exemplified. As the coherent light source 110 that emits laser light, an argon ion (Ar) laser, a helium-neon (He-Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(2) Incoherent Light Source

The incoherent light source 120 irradiates the imaging object O with incoherent light. The incoherent light denotes light which hardly has coherency like object light (object wave). Herein, it is desirable that the wavelength of the incoherent light is approximately equal to the wavelength of the coherent light emitted from the coherent light source 110. Therefore, when the incoherent light is irradiated, it is desirable to adopt a configuration capable of adjusting the wavelength of the incoherent light using a bandpass filter.

The type of the incoherent light source 120 is not particularly limited as long as the effect of the present technology is not impaired. As an example, a light emitting diode or the like may be exemplified. As other light sources, a xenon lamp, a metal halide lamp, a high pressure mercury lamp, and the like may be exemplified.

(3) Speckle Imaging Device

The imaging system 501 according to the present technology includes a speckle imaging device 130. In the speckle imaging device 130, speckle imaging is performed on the basis of scattered light obtained from the imaging object O irradiated with the coherent light.

The imaging method performed by the speckle imaging device 130 is not particularly limited as long as the effect of the present technology is not impaired, and one or two or more known imaging methods may be selected and used freely in combination. For example, an imaging method using an imaging element such as a charge coupled device (CCD) or a complementary metal oxide semiconductor (CMOS) sensor may be exemplified.

In addition, the speckle imaging device 130 may be configured to measure the luminance distribution of the speckle in the captured image. Herein, when an object illuminated by using coherent light is observed by the imaging optical system, speckle caused by scattering of the object on the image plane is observed. In the speckle imaging device 130, the luminance distribution of the speckle in the captured image is measured by using, for example, a luminance meter. In addition, it is possible to calculate the speckle luminance distribution from an image captured from an imaging element such as a CCD or a CMOS.

The method of measuring the luminance distribution is not particularly limited as long as the effect of the present technology is not impaired, and one or two or more known calculation methods may be selected and used freely in combination.

In the speckle imaging device 130, for example, an image or the like in which a pseudo blood vessel through which pseudo blood flows is mapped on the basis of the speckle luminance distribution is generated. Herein, since the speckle is a random interference/diffraction pattern as described above, when the scattering fluid such as blood moves or changes with time, the speckle also varies with time. For this reason, it is possible to observe the boundary between the fluid and other portions.

Note that, in order to further clarify the portion where speckle occurs, the speckle imaging device 130 may have a configuration where, for example, equalization is performed by using a plurality of speckle images to reduce irregularity of the speckle image.

(4) Non-Speckle Imaging Device

The imaging system 501 according to the present technology includes a non-speckle imaging device 140. In the non-speckle imaging device 140, a bright field image is captured on the basis of the reflected light obtained from the imaging object O which is irradiated with the incoherent light. Herein, since the incoherent light is light which hardly exhibits coherency, in the captured image based on the incoherent light, speckle which is a random interference/diffraction pattern does not occur. Hereinafter, for the convenience of description, a captured image where speckle does not occur is referred to as a "non-speckle image". Since the imaging method performed in the non-speckle imaging device 140 is the same as the imaging method performed in the speckle imaging device 130, the description thereof is omitted herein.

(5) Focus Detection Device

The imaging system 501 according to the present technology includes a focus detection device 150 that detects a focus for capturing the speckle image.

Since speckle is a random interference/diffraction pattern, it is difficult to identify the focus in the case of imaging the speckle. On the other hand, in a case where the image forming system is off-focused to the front side or the rear side and the imaging object O is deviated in the vertical direction from the optical axis, an interference light path which starts from one point of the imaging object O to form one speckle shape passes through a point near the optical axis on the imager with respect to the principal ray of the image forming system in the case of being off-focused to the front side and passes through a point away from the optical axis in the case of being off-focused to the rear side. As a result, in a case where the focal position for capturing the speckle image is shifted toward the user side or the rear side with respect to the focus at the time of capturing the non-speckle image, that is, the bright field image, the speckle moves in the same direction as that of the moving body or in a direction different from that of the moving body with respect to the moving body projected on the bright field image. In the following description, this phenomenon will be referred to as a "speckle correlation phenomenon".

On the basis of the speckle correlation phenomenon, the focus detection device 150 detects the focus of the speckle imaging device 130. More specifically, first, as a first step, the focal position of the speckle imaging device 130 is arranged on the further front side of the user than the focal position of the non-speckle image, and the moving direction of the speckle is identified. Next, as a second step, the focal position of the speckle imaging device 130 is arranged on the further rear side of the user than the focal position of the non-speckle image, and the moving direction of the speckle is identified. After that, while the focal position of the speckle imaging device 130 arranged on the front side or the rear side is gradually brought closer to the focal position of the non-speckle imaging device 140, a focal position at which the speckle does not move with respect to the moving body on the bright field image is detected.

In this manner, the focus detection device 150 can detect the focus of the speckle image where the speckle does not move on the image by using the correlation phenomenon of the speckle.

Herein, the detecting method is merely an example, and in the above-described method, the second step is performed after the first step. However, the first step may be performed after the second step.

(6) Combination Device

The imaging system 501 according to the present technology includes a combination device 160 as necessary. The combination device 160 combines a speckle image captured by the speckle imaging device 130 and a non-speckle image captured by the non-speckle imaging device 140. Specifically, for example, a combined image is generated by superimposing image information of the speckle image and image information of the non-speckle image.

Note that the method of generating the combined image is not particularly limited, and a known method may be adopted.

(7) Analysis Device

The imaging system 501 according to the present technology may include an analysis device 170 as necessary. The analysis device 170 analyzes the state of the imaging object O by using the speckle combined image generated by the combination device 160.

Herein, the analysis device 170 may also analyze the moving speed of the speckle by using the correlation phenomenon of the speckle observed when the focus detection device 150 detects the focus.

That is, as described above, in the speckle correlation phenomenon, the speckle moves relative to the moving body on the bright field image. For this reason, the analysis device 170 may be configured to observe the moving image in the state where the focal position of the speckle imaging device 130 is shifted from the focal position of the bright field image and to measure the moving speed of the speckle.

In such a case, for example, in a case where the imaging object O is a blood vessel, when the scattering fluid such as blood moves or changes with time, the speckle also varies with time accordingly. Therefore, the speed of the blood flow can be measured by the analysis device 170.

Note that the analysis device 170 is not necessarily included in the imaging system 501 according to the present technology, and the state of the imaging object O may also be analyzed by using an external analysis device or the like.

(8) Storage Device

The imaging system 501 according to the present technology may further include a storage device 180 that stores the speckle image captured by the speckle imaging device 130, the non-speckle image captured by the non-speckle imaging device 140, the speckle combined image generated by the combination device 160, the focus of the speckle image detected by the focus detection device 150, the analysis result analyzed by the analysis device 170, and the like.

The storage device 180 is not necessarily included in the imaging system 501 according to the present technology, but the imaging system may be connected to, for example, an external storage device to store the speckle image and the like.

(9) Focus Adjustment Device

The imaging system 501 according to the present technology includes the focus adjustment device 210. The focus adjustment device 210 performs a process of changing a focal length of the speckle imaging device 130 at the stage of detecting the focus when the focus detection device 150 captures the speckle image.

Specifically, the process performed by the focus detection device 150 of the imaging apparatus 1 according to the first embodiment, that is, the process of moving the focal position of the speckle imaging device 130 relative to the focal position of the non-speckle imaging device 140 is performed.

Then, the focus adjusted by the focus adjustment device 210 is input to the speckle imaging device 130, and thus, the speckle imaging device 130 captures the speckle image on the basis of the input information.

(10) Display Unit Device

The imaging system 501 according to the present technology may further include a display device 190 that displays the speckle image captured by the speckle imaging device 130, the non-speckle image captured by the non-speckle imaging device 140, the speckle combined image generated by the combination device 160, the analysis result analyzed by the analysis device 170, and the like. In addition, the display device 190 may display the luminance distribution measured by the speckle imaging device 130 so as to be superimposed on the speckle image. Note that the display device 190 is not necessarily included in the imaging system 501 according to the present technology, and light irradiation may be performed on the imaging object O by using, for example, an external monitor or the like.

(11) Aberration Correction Device

In the imaging system 501 according to the present technology, a speckle image is captured by the speckle imaging device 130, and a non-speckle image is captured by the non-speckle imaging device 140. That is, the imaging system 501 constitutes a compound eye imaging system. Therefore, aberration occurs between the speckle image and the non-speckle image in the imaging system 501.

In such a case, in the case of generating a combined image including the non-speckle image and the speckle image superimposed on each other, it is necessary to eliminate the aberration as much as possible. Therefore, it is desirable that the imaging system according to the present technology includes the aberration correction device 220 that corrects the aberration.

The type of aberration that can be corrected by the aberration correction device 220 is not particularly limited, and well-known aberrations such as spherical aberration, coma aberration, astigmatism, chromatic aberration (axial chromatic aberration, magnification chromatic aberration), wavefront aberration, field curvature, and deformed image may be corrected. Since the imaging apparatus according to the present technology uses two types of light sources having different wavelengths, it is desirable that the imaging apparatus is configured so as to correct, particularly, chromatic aberration among these aberrations.

Herein, the method of correcting the aberration is not particularly limited, and a known method may be adopted. For example, a method using a deformable mirror, a method of correcting the acquired image itself, or the like may be used.

The imaging system 501 according to the present technology may include an aberration measurement unit 221 that measures the aberration. In the aberration measurement unit 221, aberrations may be measured by using a known method. For example, a method of analyzing interference fringes by optical interference measurement may be considered to be adopted.

Then, the aberration measured by the aberration measurement unit 221 is input to the aberration correction device 220, and thus, the aberration correction device 220 is configured to correct the aberration on the basis of the input information.

(12) Region-Of-Interest Specification Device

The imaging system 501 according to the present technology includes a region-of-interest specification device 230 for specifying a region to be observed from the non-speckle image.

More specifically, the region-of-interest specification device 230 identifies the non-speckle image displayed by the display device 190 and selects an arbitrary region in which the user is interested in observation. After that, the region-of-interest specification device 230 detects the position information of the region of interest selected by the user. In addition, on the basis of the information on the detected region of interest, the region of interest within the imaging object O illustrated on the non-speckle image is specified.

Note that the specifying method performed by the region-of-interest specification device 230 is not particularly limited, and a known method may be used. For example, it is considered that the region-of-interest specification device 230 detects the position information of each pixel in the horizontal direction and the vertical direction of the combined image including the region of interest selected by the user and specifies the region of interest on the basis of the detected position information.

(13) Light Irradiation Adjustment Device

In a case where the imaging system 501 according to the present technology includes the region-of-interest specification device 230, it is desirable that the imaging system includes a light irradiation adjustment device 240 for irradiating the region of interest specified by the region-of-interest specification device 230 with light.

Specifically, the configuration of the light irradiation adjustment device 240 is not particularly limited, and the light irradiation adjustment device 240 is configured as, for example, a biaxial actuator that moves the incoherent light source 120 in horizontal and vertical directions and stops the incoherent light source 120.

Then, the light irradiation adjustment device 240 is configured to adjust the irradiation direction by moving the incoherent light source 120 so that the region of interest is irradiated with the incoherent light on the basis of the position information of the region of interest detected by the region-of-interest specification device 230.

According to the imaging system 501 according to the present technology, since the focus at the time of capturing the speckle image by the focus detection device 150 can be detected, it is possible to acquire the speckle image with high resolution.

In addition, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue.

Furthermore, in the imaging system 501 according to the present technology, in a case where the focus adjustment device 210 is included, since the imaging system is configured to display the speckle image captured on the basis of the focus detected by the focus adjustment device 210, it is possible to accurately grasp the moving direction of speckle with respect to the moving body on the bright field image with visual observation by using the correlation phenomenon of the speckle.

As a result, for example, in the case of imaging a blood vessel, since it is possible to accurately grasp the flowing direction of blood corpuscles, it is possible to grasp the type of blood vessel such as whether the imaged blood vessel is an artery or a vein.

In addition, in the imaging system 501 according to the present technology, in a case where the aberration correction device 220 is included, since aberration occurring between the speckle image and the non-speckle image, particularly, chromatic aberration can be corrected, it is possible to improve the resolution of the speckle image and the resolution of the non-speckle image and also to improve the resolution of the combined image including the speckle image and the non-speckle image.

As a result, for example, in a case where a blood vessel in which blood is flowing is imaged, it is possible to accurately observe the relative position of the blood vessel to the biological tissue.

Furthermore, in the imaging system 501 according to the present technology, in a case where the region-of-interest specification device 230 and the light irradiation adjustment device 240 are included, since only the region in which the user is interested can be irradiated with the incoherent light, it is possible to maximize the intensity distribution of the speckle in the region of interest in the speckle image to be captured. As a result, it is possible to generate the speckle image and, hence, the combined image with high resolution. Since the irradiation range of the incoherent light can be limited to the range of the region of interest, that is, the minimum necessary illumination intensity can be obtained, coherency of the incoherent light can be maintained constant. In addition, it is possible to reduce the adverse effect on the user due to irradiation with the incoherent light which is high in output density and harmful to the human body.

6. Imaging Method According to First Embodiment

The present technology also provides an imaging method. FIG. 7 is a flowchart of an imaging method according to the present technology. The imaging method according to the first embodiment includes at least a coherent light irradiating step, an incoherent light irradiating step, a speckle imaging step, a non-speckle imaging step, and a focus detecting step. In addition, as necessary, the imaging method may further include a combining step, an analyzing step, a storing step, a displaying step, a focus adjusting step, an aberration correcting step, a region-of-interest specifying step, and a light irradiation adjusting step. Note that, in FIG. 7, the combining step, the analyzing step, the storing step, the displaying step, the focus adjusting step, the aberration correcting step, the region-of-interest specifying step, and the light irradiation adjusting step are also illustrated, but as described above, these steps are not necessary steps. Therefore, these steps may not be performed in the imaging method according to the present technology. However, among the aforementioned steps, since a predetermined effect is exhibited by including the focus adjusting step, the aberration correcting step, the region-of-interest specifying step, and the light irradiation adjusting step, it is desirable that these steps are included. The aforementioned steps will be described below in the order of executing the imaging method according to the present technology.

(1) Incoherent Light Irradiating Step

In the imaging method according to the present technology, first, the imaging object O is irradiated with incoherent light. Herein, the type of the incoherent light source is not particularly limited as long as the effect of the present technology is not impaired. As an example, a light emitting diode or the like may be exemplified. As other light sources, a xenon lamp, a metal halide lamp, a high pressure mercury lamp, and the like may be exemplified.

(2) Aberration Correcting Step

The imaging method according to the present technology may include an aberration correcting step S2 as necessary.

In the imaging method according to the present technology, since two light beams having different wavelengths are irradiated, aberration may occur between a speckle image and a non-speckle image. Therefore, in the aberration correcting step S2, the aberration is corrected.

More specifically, in the aberration correcting step S2, first, aberration information is measured. The measurement method is not particularly limited, and a known method may be used. For example, a method of analyzing interference fringes by optical interference measurement may be considered to be adopted.

After the aberration information is measured in this manner, the aberration is corrected on the basis of the aberration information. A method of correcting aberration is not particularly limited, and a known method may be adopted. For example, a method using a deformable mirror, a method of correcting an acquired image itself, or the like may be used.

(3) Non-Speckle Imaging Step

Next, in the imaging method according to the present technology, on the basis of the reflected light obtained from the imaging object O irradiated with the incoherent light in the incoherent light irradiating step S1, a non-speckle image in which no speckle is projected, that is, a bright field image is captured.

More specifically, in the state where the aberration is corrected in the aberration correcting step S2, the non-speckle imaging step S3 is performed, so that capturing of the non-speckle image in which no aberration occurs is performed.

The imaging method in the non-speckle imaging step S3 is not particularly limited, and one or two or more known imaging methods may be selected and used freely in combination. For example, an imaging method using an imaging element such as a charge coupled device (CCD) or a complementary metal oxide semiconductor (CMOS) sensor may be exemplified.

(4) Displaying Step

The imaging method according to the present technology may include the displaying step S4 as necessary.

In this displaying step S4, the non-speckle image captured in the non-speckle imaging step S3 is displayed so as to be able to be recognized by the user.

(5) Focus Adjusting Step

The imaging method according to the present technology may include a focus adjusting step S5 as necessary. In the focus adjusting step S5, a process of changing the focal length when capturing the speckle image of the imaging object O is performed.

Specifically, the focal position in the speckle imaging device is moved relative to the focal position detected at the time of imaging in the speckle imaging step S3. For example, a process of arranging the focal position of the speckle imaging on the further front side of the user than the focal position of the non-speckle imaging or a process of arranging the focal position of the speckle imaging on the further rear side of the user than the focal position of the non-speckle imaging is performed.

(6) Focus Detecting Step

In the imaging method according to the present technology, after the focus adjusting step S5, a focus detecting step S6 is performed.

Specifically, by performing the focus adjusting step S5, a correlation phenomenon of the speckle occurs due to the nature of the speckle. That is, in a case where the focal position of the speckle imaging is moved relative to the focal position of the non-speckle imaging, the speckle moves in the same direction as that of the moving body or in a direction different from that of the moving body with respect to the moving body projected on the bright field image.

By using this, in the focus detecting step S6, an imaging position at which no speckle moves is detected as a focal position of the speckle image with respect to the moving body projected on the bright field image.

(7) Region-of-Interest Specifying Step

The imaging method according to the present technology may include a region-of-interest specifying step S7 as necessary.

In the region-of-interest specifying step S7, first, the user identifies the non-speckle image displayed in the displaying step S4 and selects an arbitrary region in which the user is interested in observation.

Specifically, the position information of the region of interest on the non-speckle image is detected, and on the basis of the position information, the region of interest within the imaging object O illustrated on the combined image is specified.

Note that the specifying method in the region-of-interest specifying step S7 is not particularly limited, and a known method may be used. For example, in the non-speckle image, a method of detecting the position information of each pixel in the horizontal direction and the vertical direction of the non-speckle image including the region of interest and specifying the region of interest on the basis of the detected position information may be considered.

(8) Light Irradiation Adjusting Step

The imaging method according to the present technology may include a light irradiation adjusting step S8 as necessary. In the light irradiation adjusting step S8, in order to irradiate the region of interest specified in the region-of-interest specifying step S7 with coherent light, an irradiation position, irradiation amount, and the like of the coherent light source are adjusted.

Desirably, the region of interest is irradiated with the coherent light on the basis of the position information of the region of interest detected in the region-of-interest specifying step S7, and the irradiation position, irradiation amount, and the like of the coherent light source are adjusted so that the intensity distribution of the speckle is maximized in the region of interest in the speckle image to be imaged.

(9) Coherent Light Irradiating Step

In the imaging method according to the present technology, after the light irradiation adjusting step S8, in the state where the irradiation position, irradiation amount, and the like of the coherent light source are adjusted in the light irradiation adjusting step S8, a coherent light irradiating step S9 of irradiating the specific region with coherent light is performed. The coherent light source is not particularly limited as long as the effect of the present technology is not impaired. As an example, laser light and the like may be exemplified. As the coherent light source that emits laser light, an argon ion (Ar) laser, a helium-neon (He—Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(10) Speckle Imaging Step

In the imaging method according to the present technology, after the coherent light irradiating step S9, speckle imaging is performed on the basis of scattered light obtained from the imaging object O irradiated with the coherent light.

The imaging method in this speckle imaging step S10 is not particularly limited, and one or two or more known imaging methods may be selected and used freely in combination. For example, an imaging method using an imaging element such as a charge coupled device (CCD) or a complementary metal oxide semiconductor (CMOS) sensor may be exemplified.

Note that, in FIG. 6, the aberration correcting step S2 is performed before the non-speckle imaging step S3. However, in order to obtain a speckle image with high resolution, it is desirable to perform the aberration correcting step S2 also before the speckle imaging step S10.

(11) Combining Step

The imaging method according to the present technology may include a combining step S11 of combining the non-speckle image captured in the non-speckle imaging step S3 and the speckle image captured in the speckle imaging step S10, as necessary.

Specifically, the speckle image is superimposed on the non-speckle image to generate a combined image. Note that the method for generating the combined image is not particularly limited, and a known method may be adopted.

(12) Analyzing Step

The imaging method according to the present technology may include an analyzing step S12 for analyzing the state of the imaging object O on the basis of the combined image generated in the combining step S11 as necessary.

In this analyzing step S12, on the basis of the relative phenomenon of the speckles detected in the focus adjusting step S5, it is possible to analyze the moving speed and the like of the scattering fluid projected as speckles.

(13) Storing Step

After the analyzing step S12 is performed, the imaging method according to the present technology may include, as necessary, a storing step S13 of storing the non-speckle image captured in the non-speckle imaging step S3, the speckle image captured in the speckle imaging step S10, the focus for capturing the speckle image detected in the focus detecting step S6, the combined image generated in the combining step S11, the analysis result in the analyzing step S12, and the like.

(14) Displaying Step

The imaging method according to the present technology may include a displaying step S14 as necessary after the storing step S13 is performed.

In this displaying step S14, the speckle image captured in the speckle imaging step S10, the focus for capturing the speckle image detected in the focus detecting step S6, the speckle combined image generated in the combining step S11, an analysis result in the analyzing step S12, and the like may be displayed so as to be able to be recognized by the user.

According to the imaging method according to the present technology, since the focus detecting step S6 is included, the focus at the time of capturing the speckle image can be detected, so that it is possible to acquire the speckle image with high resolution.

In addition, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue.

Furthermore, in the imaging method according to the present technology, in a case where the focus adjusting step S5 is included, it is possible to accurately grasp the moving direction of speckle with respect to the moving body on the bright field image with visual observation by using the correlation phenomenon of the speckle.

As a result, for example, in the case of imaging a blood vessel, since it is possible to accurately grasp the flowing direction of blood corpuscles, it is possible to grasp the type of blood vessel such as whether the imaged blood vessel is an artery or a vein.

In addition, in the imaging method according to the present technology, in a case where the aberration correcting step S2 is included, since the aberration occurring between the speckle image and the non-speckle image can be corrected, it is possible to improve the resolution of the speckle image and the resolution of the non-speckle image. In addition, it is possible to improve the resolution of the combined image including the speckle image and the non-speckle image.

As a result, for example, in a case where a blood vessel in which blood is flowing is imaged, it is possible to accurately observe the relative position of the blood vessel to the biological tissue.

Furthermore, in the imaging method according to the present technology, in a case where the region-of-interest specifying step S7 and the light irradiation adjusting step S8 are included, since only the region in which the user is interested can be irradiated with the incoherent light, it is possible to maximize the intensity distribution of the speckle in the region of interest in the speckle image to be captured. As a result, it is possible to generate the speckle image and, hence, the combined image with high resolution. Since the irradiation range of the incoherent light can be limited to the range of the region of interest, that is, the minimum necessary illumination intensity can be obtained, coherency of the incoherent light can be maintained constant. In addition, it is possible to reduce the adverse effect on the user due to irradiation with the incoherent light which is high in output density and harmful to the human body.

In addition, the imaging apparatus according to the present technology may also have the following configurations.

(1)

An imaging apparatus, including:

a coherent light source that irradiates an imaging object with coherent light;

an incoherent light source that irradiates the imaging object with incoherent light;

a speckle imaging unit that captures a speckle image obtained from scattered light of the imaging object irradiated with the coherent light;

a non-speckle imaging unit that captures a non-speckle image obtained from reflected light of the imaging object irradiated with the incoherent light; and a focus detection unit that detects a focus of the speckle imaging unit on the basis of a focal position of the non-speckle imaging unit.

(2)

The imaging apparatus according to (1), further including:

a focus adjustment unit that adjusts a focal length of the speckle imaging unit with respect to a focus of the non-speckle imaging unit; and a display unit that displays the speckle image captured on the basis of the focus adjusted by the focus adjustment unit.

(3)

The imaging apparatus according to (1), further including an aberration correction unit that corrects aberration occurring between the non-speckle imaging unit and the speckle imaging unit.

(4)

The imaging apparatus according to (3), in which the aberration correction unit corrects chromatic aberration.

(5)

The imaging apparatus according to (1), further including:

a region-of-interest specification unit that specifies an arbitrary region of interest in the non-speckle image captured by the non-speckle imaging unit; and a light irradiation adjustment unit that adjusts an irradiation position of the coherent light source on the basis of specification information of the region of interest by the region-of-interest specification unit.

In addition, the imaging system according to the present technology may also have the following configurations.

(6)

An imaging system, including: a coherent light source that irradiates an imaging object with coherent light;

an incoherent light source that irradiates the imaging object with incoherent light;

a speckle imaging device that captures a speckle image obtained from scattered light of the imaging object irradiated with the coherent light;

a non-speckle imaging device that captures a non-speckle image obtained from reflected light of the imaging object irradiated with the incoherent light; and a focus detection device that detects a focus of the speckle imaging device on the basis of a focal position of the non-speckle imaging device.

(7)

The imaging system according to (6), further including:

a focus adjustment device that adjusts a focal length of the speckle imaging device with respect to a focus of the non-speckle imaging device; and a display device that displays the speckle image captured on the basis of the focus adjusted by the focus adjustment device.

(8)

The imaging system according to (6), further including an aberration correction device that corrects aberration occurring between the non-speckle imaging device and the speckle imaging device.

(9)

The imaging system according to (8), in which the aberration correction device corrects chromatic aberration.

(10)

The imaging system according to (6), further including:

a region-of-interest specification device that specifies an arbitrary region of interest in the non-speckle image captured by the non-speckle imaging device; and a light irradiation adjustment device that adjusts an irradiation position of the coherent light source on the basis of specification information of the region of interest by the region-of-interest specification device.

Reference Signs List 1, 101, 201, 301, 401 imaging apparatus
11 coherent light source
12 incoherent light source
13 speckle imaging unit
14 non-speckle imaging unit
15 focus detection unit

The invention claimed is:

1. An imaging system, comprising:
   a speckle imaging unit that captures a speckle image obtained from scattered light of an imaging object irradiated with coherent light;
   a non-speckle imaging unit that captures a non-speckle image obtained from reflected light of the imaging object irradiated with incoherent light; and
   a focus determination unit that determines a focus of the speckle imaging unit on the basis of a focal position of the non-speckle imaging unit.

2. The imaging system according to claim 1, further comprising:
   a focus adjustment unit that adjusts a focal length of the speckle imaging unit with respect to a focus of the non-speckle imaging unit; and
   a display unit that displays the speckle image captured on the basis of the focus adjusted by the focus adjustment unit.

3. The imaging system according to claim 1, further comprising
   an aberration correction unit that corrects aberration occurring between the non-speckle imaging unit and the speckle imaging unit.

4. The imaging system according to claim 3, wherein the aberration correction unit corrects chromatic aberration.

5. The imaging system according to claim 1, further comprising:
   a coherent light source that irradiates the imaging object with the coherent light; and
   an incoherent light source that irradiates the imaging object with the incoherent light.

6. The imaging system according to claim 5, further comprising:
   a region-of-interest specification unit that specifies an arbitrary region of interest in the non-speckle image captured by the non-speckle imaging unit; and
   a light irradiation adjustment unit that adjusts an irradiation position of the coherent light source on the basis of specification information of the region of interest by the region-of-interest specification unit.

7. The imaging system according to claim 5, wherein the coherent light and the incoherent light are guided through a medical observation apparatus and irradiate the imaging object.

8. The imaging system according to claim 7, wherein the medical observation apparatus comprises at least one of an endoscope and a microscope.

9. The imaging system according to claim 1, wherein the imaging object includes a living body or blood vessels.

10. An imaging method, comprising:
    a speckle imaging step of capturing a speckle image obtained from scattered light of an imaging object irradiated with coherent light;
    a non-speckle imaging step of capturing a non-speckle image obtained from reflected light of the imaging object irradiated with incoherent light; and
    a focus determining step of determining a focus for capturing the speckle image on the basis of a focal position in the non-speckle imaging step.

11. The imaging method according to claim 10, further comprising:
    a coherent light irradiating step of irradiating the imaging object with the coherent light; and
    an incoherent light irradiating step of irradiating the imaging object with the incoherent light.

12. The imaging method according to claim 11, further comprising:
    guiding the coherent light and the incoherent light through a medical observation apparatus and irradiating the imaging object.

13. The imaging method according to claim 12, wherein the medical observation apparatus comprises at least one of an endoscope and a microscope.

14. The imaging method according to claim 10, wherein the imaging object includes a living body or blood vessels.

15. The imaging method according to claim 10, further comprising:
    a focus adjustment step of adjusting a focal length of the speckle imaging step with respect to a focus of the non-speckle imaging step; and
    a display step of displaying the speckle image captured on the basis of the focus adjusted in the focus adjustment step.

16. The imaging method according to claim 10, further comprising:
    an aberration correction step of correcting aberration occurring between the non-speckle imaging step and the speckle imaging step.

17. The imaging method according to claim 16, wherein the aberration correction step corrects chromatic aberration.

18. The imaging method according to claim 10, further comprising:
    a region-of-interest specification step of specifying an arbitrary region of interest in the non- speckle image captured in the non-speckle imaging step; and
    a light irradiation adjustment step of adjusting an irradiation position of a coherent light source on the basis of specification information of the region of interest specified by the region-of- interest specification step.

* * * * *